United States Patent
Au et al.

(10) Patent No.: US 7,465,323 B2
(45) Date of Patent: Dec. 16, 2008

(54) HIGH CARBONATE OXIDATIVE DYE COMPOSITIONS

(75) Inventors: Van Au, Naperville, IL (US); Jitendra Patel, Fox River Grove, IL (US)

(73) Assignee: Conopco, Inc., Englewood Cliffs, NJ (US)

( * ) Notice: Subject to any disclaimer, the term of this patent is extended or adjusted under 35 U.S.C. 154(b) by 260 days.

(21) Appl. No.: 11/345,896

(22) Filed: Feb. 2, 2006

(65) Prior Publication Data

US 2007/0174976 A1    Aug. 2, 2007

(51) Int. Cl.
*A61Q 5/10* (2006.01)

(52) U.S. Cl. .................... 8/405; 8/406; 8/435; 8/552; 8/561; 8/584; 8/594; 8/606; 8/611; 8/620

(58) Field of Classification Search ............ 8/405, 8/406, 435, 552, 561, 584, 594, 606, 611, 8/620
See application file for complete search history.

(56) References Cited

U.S. PATENT DOCUMENTS

| | | |
|---|---|---|
| 2002/0189034 A1 | 12/2002 | Kitabata et al. |
| 2004/0010865 A1 | 1/2004 | Ogawa et al. |
| 2004/0019980 A1 | 2/2004 | Au et al. |
| 2004/0098814 A1 | 5/2004 | Au et al. |
| 2004/0098816 A1 | 5/2004 | Au et al. |
| 2004/0237218 A1 | 12/2004 | Marsh et al. |
| 2005/0086748 A1 | 4/2005 | Rondeau et al. |
| 2005/0226838 A1* | 10/2005 | Krause et al. ............ 424/70.13 |
| 2006/0117493 A1* | 6/2006 | Bureiko et al. ................ 8/405 |

FOREIGN PATENT DOCUMENTS

EP     0 312 343 B1    4/1989

OTHER PUBLICATIONS

"Structure® XL A New Concept for Creating and Processing, Elegant and Stable Emulsions"—National Starch Personal Care Product Literature, 2002.
Structure® XL A New Concept To Simply Create and Process Elegant and Stable Personal Care Formulations—National Starch Personal Care Product Literature, 2002.
U.S. Appl. No. 11/025,295 to Au et al, filed Dec. 29, 2004, entitled One Step Hair Coloring Using Salts.

* cited by examiner

*Primary Examiner*—Eisa B Elhilo
(74) *Attorney, Agent, or Firm*—Karen E. Klumas

(57) ABSTRACT

A storage stable dye composition having a pH of from 9 to 11, the dye composition comprising:
(a) oxidation dye precursor,
(b) at least 8 wt % of carbonate salt,
(c) at least 2 wt. % of a fatty phase comprising fatty alcohol and quaternary conditioning agent,
(d) hydroxypropyl starch phosphate, and
(e) carrier,
wherein the quaternary conditioning agent is present in the dye composition in an amount of at least 0.5 wt. %, and wherein the ratio of fatty alcohol to quaternary conditioning agent is 4:1 to 0.5:1.

Hair coloring compositions formed from such dye compositions, as well as methods of coloring hair using such hair coloring compositions, are also disclosed.

13 Claims, No Drawings

HIGH CARBONATE OXIDATIVE DYE COMPOSITIONS

FIELD OF THE INVENTION

This invention relates to storage-stable dye compositions which comprise relatively high levels of carbonate salt. This invention also relates to hair coloring compositions formed from such dye compositions, methods of coloring hair using such hair coloring compositions, and hair coloring kits comprising such hair dye compositions.

BACKGROUND OF THE INVENTION

To color human or animal hair using conventional oxidative dye technology, a mixture of suitable oxidative coloring agents and at least one oxidizing agent or developer, typically hydrogen peroxide, is commonly employed. Hair colorants based on oxidative dyes generally have two parts, i.e., a dye component and a developer component, each of which is ordinarily provided in a liquid or other fluid form, e.g., gel. Just before use, the dye and developer components are mixed together to form the colorant composition. The kits in which these components are provided include dye systems known as "box colorants", which are generally formulated as single-use products. Box colorants include kits for home as well as salon use.

Carbonates are among the ingredients that have been disclosed for use in hair colorant compositions based on oxidative dyes. For example, carbonates have been disclosed for use as buffers or pH adjusters. As a buffer or pH adjuster, carbonates are used in relatively small amounts, typically not exceeding 1% by weight of the colorant composition after mixing. Other uses of carbonates in hair colorant compositions have been disclosed.

U.S. Patent Application Publication No. 2004/0019980, published Feb. 5, 2004, discloses a hair coloring composition comprising two compositions which are mixed just prior to application to the hair:
  (a) a composition comprising a water-soluble peroxygen oxidizing agent; and
  (b) a composition comprising one or more oxidative hair coloring agents selected from the group consisting of an aromatic diamine, an amino phenol, a naphthol, a polyhydric phenol, a catechol and mixtures thereof; wherein the composition comprising one or more oxidative hair coloring agents further comprises at least one water soluble carbonate releasing salt; and optionally a water soluble ammonium salt.

In Example 1, hair coloring compositions having 1.0-5.0% by weight of water soluble carbonate releasing salt and 0-5.0% by weight of water soluble ammonium salt are disclosed.

U.S. Patent Application No. 2002/0189034, published Dec. 19, 2002, discloses a two-agent hair dyeing/bleaching composition comprising a primary agent containing an alkali agent and a secondary agent containing an oxidizing agent, wherein the primary agent contains: (a) at least one alkali agent selected from the group consisting of ammonia water and monoethanolamine, (b) at least one water-soluble ammonium salt selected from the group consisting of ammonium carbonate and ammonium hydrogencarbonate, and (c) at least one first pH adjuster selected from the group consisting of polycarboxylic acids and their salts. At paragraph 0026, it is disclosed that that the primary agent "preferably contains the alkali agent of component (a) at 1-25 wt. (where the ammonia water weight is expressed in terms of ammonia water at a concentration of 28 wt. %), the water-soluble ammonium salt of component (b) at 0.5-20 wt. % and the first pH adjuster component (c) at 0.1-10 wt. %." At paragraph 0043 the application notes that the composition may additionally contain a hair dye when it is to be used as a "dyeing agent".

U.S. Patent Application Publication No. 2004/0010865, published Jan. 22, 2004, discloses hair dye compositions having a pH of from 8.5-12 which comprise (A) ammonia or an ammonium salt, (B) a carbonate (other than an ammonium salt), (C) a transition metal salt, and (D) a chelating agent. The content of ingredients (A) and (B) in the composition are given as 0.01 to 3 mol/kg and 0.001 to 1 mol/kg, respectively. It is further disclosed that the compositions "do not give off an intensely irritating odor and have low irritating property, can change hair into a lighter tone in a short time or can dye hair well in a color ranging from a light color to a deep color, and moreover, assure good retention of the thus-obtained tone or color".

U.S. Patent Application Publication No. 2004/0098814, published May 27, 2004 discloses a method for the gradual permanent coloring of hair through the use of daily hair care compositions. In the method therein described, the hair is contacted for a period of about 5 seconds to about 5 minutes with a recently prepared mixture of compositions referred to as Parts A and B. Part A is a dye composition in a shampoo or conditioner base at alkaline pH and Part B is a peroxide such as hydrogen peroxide in a conditioner or shampoo base at acidic pH. More particularly, Part A is a mixture of (I) a dye intermediate in a shampoo or conditioner base and a salt component (II) as therein more particularly described. The salt component II is a water soluble ammonium carbonate or carbamate salt at about 0.1% to about 15%, more preferably about 1% to about 10% or a combination of i) a water soluble carbonate releasing salt at about 0.1 % to about 15%, more preferably about 1% to about 10% and ii) a water soluble ammonium salt at about 0.1% to about 15%, more preferably about 1% to about 10%.

U.S. Patent Application Publication No. 2004/0098816, published May 27, 2004, discloses a method for the gradual permanent coloring of hair with longer lasting conditioning and with minimized hair damage through the use of daily hair care compositions. In the method therein described, hair is subjected to a number of treatments, having a set time interval between each two consecutive treatments, wherein each treatment comprises:
  a) contacting the hair with a recently prepared mixture of a colorant composition comprising:
    A) an alkaline dye composition comprising:
      i) an effective amount to color hair of at least one dye intermediate;
      ii) from about 0.1 to about 25% by weight based on the colorant composition of a water soluble ammonium carbonate or carbamate salt;
      iii) from 1 to 5% by weight based on the colorant composition of a chelant; and
      iv) a cosmetically acceptable carrier; and
    B) an oxidizing composition comprising:
      i) from 0.1 to 15% by weight based on the coloring composition of a peroxide compound; and
      ii) a cosmetically acceptable carrier; and
  b) rinsing the mixture from the hair with water.

U.S. Patent Application Publication No. 2004/0237218, published Dec. 2, 2004, discloses hair coloring and bleaching compositions comprising:
  i) at least one source of peroxygen monoalkanoate ions;
  ii) at least one alkalizing agent, preferably a source of ammonium ions; and iii) at least one radical scavenger, wherein said composition has a pH of up to 9.5, which compositions are disclosed as providing "high level of lift and lightening and the required dye deposition and grey coverage whilst reducing the concentration of peroxide, the ammonia odour and inducing the hair fibre damage.

The application characterizes colorants that utilize an ammonia or alkanolamine alkalizer as typically having an optimal pH of about 10.0, stating: "This high pH is necessary in order to produce a sufficient concentration of the perhydroxy anion (HOO—) to give the desired bleaching of melanin. . . . However, . . . compositions having a high pH cause many of the disadvantages noted by consumers of these colourant systems. In particular the level of the volatile ammonia increases at high pH (above 9.5) giving increased unpleasant odour. Furthermore, reactive species including the perhydroxy anion reacts with the hair fibre resulting in significant fibre damage." See paragraphs 0028 to 0030. The application discloses that the addition of a radical scavenger removes and/or reactivates which are referred to as "harmful carbonate radicals" and transforms them to "relatively harmless species". The application discloses hair coloring compositions having a pH of up to and including 9.5. At paragraph 0062 the application states: "Preferably, the compositions of the present invention have a pH of fro about 9.5 to about 7.5, more preferably from about 9.5 to about 8.4 and most preferably from about 9.4 to about 8.5 and even more preferably about pH 9.0." Exemplified by the application are hydrogen peroxide-containing formulations that contain from 2.0 to 8.0 wt. % of carbonate (as ammonium carbonate, potassium carbonate, or a combination thereof). Two of exemplified formulations, emulsion formulation 20, and thickened aqueous solution 10, both of which were reported to have been adjusted to a pH of 9.0, also contain 2.0 wt. % of hydroxypropyl starch phosphate. Thickened aqueous solution 10 lacked both a quaternary conditioning agent and fatty alcohol; emulsion 20 contained 3.0 wt. % Crodafos® CES (reported in the literature to be a mixture of cetearyl alcohol, dicetyl phosphate and ceteth 10 phosphate), but lacked a quaternary conditioning agent Owing to the instability of peroxide in the presence of base, the developer component of peroxide-based hair colorant systems or kits is normally formulated to an acidic pH. At acidic pHs, carbonates are susceptible to decomposition. Accordingly, when present, carbonates are generally formulated as part of the colorant system's dye component or "tint", rather than its developer component. To minimize weight and the cost of additional ingredients needed to compensate for dilution effects, the amount of solvent provided to the dye component is generally kept relatively low. Solubility limitations and other formulation constraints limit the amount of carbonate that can be contained in the dye component of colorant composition systems. At levels in excess of about 6 percent by weight, carbonates tend to precipitate or "salt out" of the developer component and can give rise to other stability issues, e.g., breaking of emulsions, undesirable viscosity changes, and the like. The difficulty in formulating storage stable dye compositions containing high levels of carbonate salt is exacerbated when the dye composition further comprises at least 2 wt % of a fatty phase comprising fatty alcohol and conditioning quat.

Various materials have been suggested as rheology modifiers and emulsion stabilizers. The rheology modifying properties of a material are typically not predictive of the ability of a material to inhibit phase separation in high salt content compositions, particularly in emulsion compositions that comprise a fatty phase comprising a fatty alcohol and conditioning quat, particularly when the fatty phase is present in an amount of at least 2 wt. %, more particularly at least 4 wt. %. Finding an additive that inhibits. phase separation in high salt content dye compositions having such a fatty phase has long eluded formulators.

U.S. patent application Ser. No. 11/025,295, filed Dec. 29, 2004, discloses that the use of relatively high levels of at least one ammonium carbonate salt in combination with relatively high levels of at least one additional soluble carbonate salt other than an ammonium carbonate salt, and a relatively high level of chelating agent provides colorant compositions having superior lift and dyeing properties. The difficulty in formulating high carbonate compositions is avoided through the use of a separate salt component. The application discloses coloring compositions comprising the following individual components, which components are combined just prior to application to the hair:

(a) a dye component comprising oxidation dye precursor,
(b) a developer component comprising peroxide-releasing compound, and
(c) a salt component comprising carbonate-releasing salt, wherein the dye, developer and salt components are formulated to provide the hair coloring composition with: (i) at least one ammonium carbonate salt and at least one additional soluble carbonate salt other than an ammonium carbonate salt, wherein the ratio, by weight, of ammonium carbonate salt to additional soluble carbonate salt is from about 1:0.6 to about 1:1.6, (ii) a total soluble carbonate salt content of greater than about 10% by weight, based on the combined weight of the dye, developer and salt components, and (iii) at least about 1% by weight of chelating agent, based on the combined weight of the dye, developer and salt components.

It is an object of this invention to improve the storage stability of dye compositions comprising (a) oxidation dye precursor, (b) relatively high levels of carbonate salt, i.e., at least 8 weight percent, preferably at least 10 weight percent, and (c) a fatty phase comprising fatty alcohol and conditioning quat. It is yet another object of this invention to maximize the deposition of conditioning quat from hair colorants formed from such dye compositions. In at least one embodiment, it is yet a further object of this invention to provide a dye composition having a pH of at least 9.5, more particularly, in excess of 9.5.

SUMMARY OF THE INVENTION

It has been found that the incorporation of a hydroxypropyl starch phosphate into dye compositions comprising (a) oxidation dye precursor, (b) relatively high levels of carbonate salt, and (c) a fatty phase comprising fatty alcohol and quaternary conditioning agent improves the storage stability and reduces the tendency of such compositions toward separation of the conditioning phase. Without wishing to be bound to theory, it is believed that enhancing the solubility of the salt in such compositions minimizes disruption of the fatty phase which, in turn, aids in the deposition of the quaternary conditioning agent in hair colorants formed from such compositions, particularly when the dye composition contains relative amounts of fatty alcohol and quaternary conditioning agent as hereinafter described.

In a preferred embodiment there is provided dye compositions wherein the fatty phase is present in an amount of at least 4 wt. %, more particularly, at least 6 wt. %.

In one embodiment of the subject invention there is provided a dye composition having a pH of from 9 to 11, the dye composition comprising:

(a) oxidation dye precursor,
(b) at least 8 wt %, preferably from 8 to 20 wt. %, more preferably from 10 to 20 wt. %, of carbonate salt,
(c) at least 2 wt. %, preferably from 4 to 15 wt. %, more preferably from 6 to 10 wt. %, of a fatty phase comprising fatty alcohol and quaternary conditioning agent,
(d) hydroxypropyl starch phosphate, and
e) carrier,
wherein the quaternary conditioning agent is present in the dye composition in an amount of at least 0.5 wt. %, preferably from 1 to 8 wt. %, more preferably from 2 to 6 wt. %, and wherein the ratio of fatty alcohol to quaternary conditioning agent is 4:1 to 0.5:1.

In a further embodiment there is provided a hair coloring composition formed by mixing a dye composition as described by this invention with a developer comprising at least one peroxide-releasing compound in a suitable cosmetically acceptable carrier. In yet another embodiment there is provided a method of coloring hair using the hair coloring composition of this invention.

In yet another embodiment there is provided a hair coloring kit comprising as separately packaged components:
(A) a dye composition as described by this invention,
(B) a developer comprising at least one peroxide-releasing compound in a suitable cosmetically acceptable carrier, wherein the kit further comprises directions instructing that the dye and developer are combined just prior to use to form a hair coloring composition.

DETAILED DESCRIPTION OF THE INVENTION

As used herein %, wt. %, or weight % refers to the percent by weight of an ingredient as compared to the total weight of the composition or component that is being discussed. Except in the operating and comparative examples, or where otherwise explicitly indicated, all numbers in this description indicating amounts of materials, material ratios, or physical properties are to be understood as modified by the word "about".

Throughout the specification and claims, the terms "dye composition" and "dye component" are, with reference to the subject invention, used interchangeably to refer to the dye precursor-containing composition prior to its combination with developer. As distinguished from the dye composition, the terms "hair coloring composition", "hair colorant" and "hair colorant composition" refer to the composition formed by the mixing of the dye composition with developer.

The term "carbonate salt" refers to soluble carbonate, bicarbonate and carbamate salts, as well as to compounds and combinations of compounds that release soluble carbonate upon metathesis. Examples of carbonate salts include, but are not limited to. ammonium carbonate, ammonium bicarbonate, ammonium carbamate, alkali metal carbonates and bicarbonates, guanidine carbonate, and the like, and mixtures of one or more thereof. In the practice of this invention the use of ammonium carbonate, as well as combinations of ammonium carbonate and one or more alkali metal carbonates, in particular sodium carbonate, is of particular interest.

The dye compositions of this invention are formulated to comprise carbonate salt in an amount of at least 8 wt. %, preferably at least 10 wt. %. In one embodiment of interest the dye compositions comprise from 8 to 20 wt. %, more particularly from 10 to 20 wt. %, of carbonate salt. In at least one embodiment of this invention, the carbonate salt is present in the dye composition in an amount of from 13 to 20 wt. %, more particularly, from 15 to 20 wt %. Dye compositions comprising from 10 to 15% of carbonate salt are also of interest in at least one embodiment of the subject invention.

The colorant compositions of this invention comprise one or more oxidation dye precursors that upon reaction with a peroxide compound such as, for example, hydrogen peroxide, form materials capable of delivering color to the hair. Precursors known as "primary intermediates" produce colors when oxidized. Another class of precursors, known as "couplers" or "secondary intermediates", form reactive dye species when oxidized in the presence of a primary intermediate but, in general, do not produce any color when oxidized alone. The coupler is utilized to expand the color range by reaction with the primary intermediate, and may also be used to accelerate color formation. Oxidation dye precursors (primary intermediates and couplers) are described, for example, in Sagarin, "Cosmetic Science and Technology", Interscience, Special Edition, Volume 2, pages 308 to 310; and "The Chemistry of Synthetic Dyes", Volume 5, Academic Press, Inc., New York and London (1971).

Non-limiting examples of precursors suitable for use herein and which may function as primary intermediates are the following: 1,4-diamino-benzene (p-phenylenediamine); 1,4-diamino-2-methyl-benzene (p-toluylenediamine); 1,4-diamino-2,6-dimethyl-benzene; 1,4-diamino-3,5-diethylbenzene; 1,4-diamino-2,5-dimethyl-benzene; 1,4-diamino-2,3-dimethylbenzene; 2-chloro-1,4-diaminobenzene; 1,4-diamino-2-(thiophen-2-yl)benzene; 1,4-diamino-2-(thiophen-3-yl)benzene; 1,4-diamino-2-(pyridin-3-yl) benzene; 2,5-diaminobiphenyl; 1,4-diamino-2-methoxymethyl-benzene; 1,4-diamino-2-aminomethylbenzene; 1,4-diamino-2-hydroxymethylbenzene; 1,4-diamino-2-(2-hydroxyethoxy)benzene; 2-(2-(acetylamino)ethoxy)-1,4-diaminobenzene; 4-phenylaminoaniline; 4-dimethylamino-aniline; 4-diethylamino-aniline; 4-dipropylamino-aniline; 4-[ethyl(2-hydroxyethyl)amino]-aniline; 4-[di(2-hydroxyethyl)amino]-aniline; 4-[di(2-hydroxyethyl)amino]-2-methyl-aniline; 4-[(2-methoxyethyl) amino]-aniline; 4-[(3-hydroxypropyl)amino]-aniline; 4-[(2,3-dihydroxypropyl)amino]-aniline; 1,4-diamino-2-(2-hydroxyethyl)-benzene; 1,4-diamino-2-(1-methylethyl)-benzene; 1,3-bis[(4-aminophenyl)(2-hydroxyethyl)amino]-2-propanol; 1,4-bis[(4-aminophenyl)amino]-butane; 1,8-bis (2,5-diaminophenoxy)-3,6-dioxaoctane; 4-amino-phenol; 4-amino-3-methyl-phenol; 4-amino-3-(hydroxymethyl)-phenol; 4-amino-3-fluoro-phenol; 4-methylamino-phenol; 4-amino-2-(aminomethyl)-phenol; 4-amino-2-(hydroxymethyl)-phenol; 4-amino-2-fluorophenol; 4-amino-2-[(2-hydroxyethyl)-amino]methylphenol; 4-amino-2-methyl-phenol; 4-amino-2-(methoxymethyl)-phenol; 4-amino-2-(2-hydroxyethyl)-phenol; 5-amino-salicylic acid; 2,5-diaminopyridine; 2,4,5,6-tetraamino-pyrimidine; 4,5-diamino-1-1(2-hydroxyethyl)-1H-pyrazole; 4,5-diamino-1-(1-methylethyl)-1H-pyrazole; 4,5-diamino-1-[(4-methylphenyl)methyl]-1H-pyrazole; 1-[(4-chlorophenyl) methyl]-4,5-diamino-1H-pyrazole; 4,5-diamino-1-methyl-1H-pyrazole; 2-aminophenol; 2-amino-6-methylphenol; and 2-amino-5-methylphenol.

Non-limiting examples of couplers suitable for use herein are the following: N-(3-dimethylamino-phenyl)-urea; 2,6-diamino-pyridine; 2-amino4-[(2-hydroxyethyl)amino]anisole; 2,4-diamino-1-fluoro-5-methylbenzene; 2,4-diamino-1-methoxy-5-methylbenzene 2,4-diamino-1-ethoxy-5-methylbenzene; 2,4-diamino-1-(2-hydroxyethoxy)-5-methylbenzene; 2,4-di[(2-hydroxyethyl)amino]-1,5-dimethoxybenzene; 2,3-diamino-6-methoxy-pyridine; 3-amino-6-methoxy-2-(methylamino)pyridine; 2,6-diamino-3,5-dimethoxypyridine; 3,5-diamino-2,6-dimethoxypyridine; 1,3-diaminobenzene; 2,4-diamino-1-(2-hydroxyethoxy)benzene; 1,3-diamino-4-(2,3-hydroxpropoxy)

benzene; 2,4-diamino-1,5-di(2-hydroxyethoxy)-benzene; 1-(2-aminoethoxy)-2,4-diaminobenzene; 2-amino-1-(2-hydroxyethoxy)-4-methylaminobenzene; 2,4-diaminophenoxyacetic acid ester; 3-[di(2-hydroxyethyl)amino]aniline; 4-amino-2-di[(2-hydroxyethyl)amino]-1-ethoxy-benzene; 5-methyl-2-(1-methylethyl)phenol; 3-[(2-hydroxyethyl)amino]aniline; 3-[(2-aminoethyl)amino]aniline; 1,3-di(2,4-diaminophenoxy)propane; di(2,4-diaminophenoxy)methane; 1,3-diamino-2,4-dimethoxybenzene; 2,6-bis(2-hydroxyethyl)aminotoluene; 4-hydroxyindole; 3-dimethylaminophenol; 3-diethylaminophenol; 5-amino-2-methylphenol; 5-amino-4-fluoro-2-methyl-phenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methyl-phenol; 3-amino-2-chloro-6-methylphenol; 3-aminophenol; 2-[(3-hydroxyphenol)-amino]acetamide; 5-[(2-hydroxyethyl)amino]4-methoxy-2-methylphenol; 5-[(2-hydroxyethyl)amino]-2-methylphenol; 3-[(2-hydroxyethyl)amino]-phenol; 3-[(2-methoxyethyl)amino]-phenol; 5-amino-2-ethyl-phenol; 5-amino-2-methoxyphenol; 2-(4-amino-2-hydroxyphenoxy)ethanol; 5-[(3-hydroxypropyl)amino]-2-methylphenol; 3-[(2,3-dihydroxypropyl)amino]-2-methylphenol; 3-[(2-hydroxyethyl)amino]-2methylphenol; 2-amino-3-hydroxypyridine; 5-amino4-chloro-2-methylphenol; 1-naphthol; 2-methyl-1-naphthol; 1,5-dihydroxynaphthalene; 1,7-dihydroxy-naphthalene; 2,3-dihydroxynaphthalene, 2,7-dihydroxy-naphthalene; 2-methyl-1-naphthol-acetate; 1,3-dihydroxybenzene; 1-chloro-2,4-dihydroxy-benzene; 2-chloro-1,3-dihydroxybenzene; 1,2-dichloro-2,4-dihydroxy-4-methylbenzene; 1,5-dichloro-2,4-dihydroxy-benzene; 1,3-dihydroxy-2-ethyl-benzene; 3,4-methylenedioxy-phenol; 3,4-methylenedioxy-aniline; 6-bromo-1-hydroxy-3,4-methylenedioxybenzene; 3,4-diaminobenzoic acid; 3,4-dihydroxy-6-hydroxy-1,4(2H)benzoxazine; 6-amino-3,4-dihydro-1,4(2H)-benzoxazine; 3-methyl-1-phenyl-5-pyrazolone; 5,6-dihydroxyindole; 5,6-dihydroxyindoline; 5-hydroxyindole; and 6-hydroxyindole.

The descriptions of primary intermediates and couplers given above is meant implicitly to include the salt forms of those dye molecules that form stable salts.

The oxidation dye precursor generally comprises from about 0.01 to about 20 percent by weight, more particularly from about 0.1 to about 15 percent by weight of the dye component. In at least one embodiment of interest, the oxidation dye precursor comprises from about 0.1 to about 10 percent by weight of the dye component. In another embodiment of interest, the oxidation dye precursor comprises from about 0.1 to about 5 percent by weight of the dye component.

Additionally, the dye compositions of this in invention may optionally include non-oxidative and other dye materials. Optional non-oxidative and other dyes suitable for use here include semi-permanent, temporary and other dyes. Non-oxidative dyes as defined herein in include the so-called "direct action dyes", metallic dyes, metal chelate dyes, fiber reactive dyes and other synthetic and natural dyes. Various types of non-oxidative dyes are described, for example, in "The Science of Hair Care", edited by C. Zviak, Chapter 7 (pp. 235-261); and "Hair Dyes", J. C. Johnson, Noyes Data Corp., Park Ridge, U.S.A. (1973) (pp. 3-91 and 113-139).

Desirably, the dye component is formulated to a pH of from 9 to 11, typically through the inclusion of one or more alkalizing agents. Examples of such alkalizing agents include, but are not limited to: ammonium hydroxide, alkali metal hydroxides and alkaline earth metal hydroxides; amines such as for example, alkanolamines, polyalkylene amines, heterocyclic amines; basic amino acids; and the like. Non-limiting examples of alkalizing agents suitable for use herein are: ammonium hydroxide, sodium hydroxide, potassium hydroxide, magnesium hydroxide, calcium hydroxide, urea, ethylamine, dipropyl amine, triethylamine, 1,3-diaminopropane, monoethanolamine, diethanolamine, triethanolamine, dimethylaminoethanol, diethylenetriamine, morpholine, diethylaminoethanol, aminoalkylpropanediol, L-arginine, lysine, oxylysine, and histidine. Preferred alkalizing agents are ammonium and/or sodium hydroxide. Optionally, one or more buffering agents may also be included within the dye composition to assist in maintaining a desired pH. In one embodiment of this invention the dye composition is formulated to a pH of 9.5 to 11, more particularly, 9.5 to 10.5. In at least one embodiment of interest the dye composition is formulated to a pH in excess of 9.5. In another embodiment of interest the dye composition is formulated to a pH of in excess of 9.5, but less than 11.

The dye compositions of this invention comprise at least 2 wt. %, preferably at least 4 wt. %, of a fatty phase comprising fatty alcohol and cationic conditioning agent. Dye compositions wherein the fatty phase is present in an amount of from 4 to 15 wt. %, more particularly from 6 to 10 wt. % are of particular interest in at least one embodiment of this invention. The fatty phase may further comprise one or more additional materials that are compatible with the fatty alcohol and cationic conditioning agent components thereof, such as for example, additional conditioning agents (including, but not limited to, volatile and non-volatile silicones), fragrance oils, and the like.

In at least one embodiment, the fatty alcohol and cationic conditioning agent combined comprise from 60 to 100% more particularly, from 70 to 100% of the fatty phase of the dye composition. Dye compositions wherein the fatty alcohol and cationic conditioning agent comprise from 65 to 95 wt. %, of the fatty phase, more particularly from 65 to 90 wt. % of the fatty phase, are of interest in at least one embodiment of this invention.

Fatty alcohols suitable for use herein class includes long chain ($C_{12}$-$C_{22}$) fatty alcohols. Non-limiting examples include: lauryl alcohol, oleyl alcohol, myristyl alcohol, stearyl alcohol, and cetearyl alcohol, and mixtures thereof. In addition to their thickening properties, the fatty alcohols function, in part, as conditioning agents and, together under the conditioning quat, form a conditioning gel phase. Optionally, the fatty alcohols may be in alkoxylated form. Desirably, such alkoxylates will contain an average of one to three, more particularly one to two alkylene oxide, preferably ethylene oxide units. Preferably such alkylene oxide units are ethylene oxide units. The fatty alcohol, including any alkoxylated fatty alcohols which may also be present, is desirably present in the dye compositions of this invention in an amount of from 1 to 15 weight %, preferably from 2 to 10 weight % and, in at least one embodiment of particular interest, in an amount of from 4 to 10 weight %, more particularly from 4 to 8 wt. %.

The term "conditioning quat" is herein used interchangeably with and as an alternative to the term "quaternary conditioning agent". The fatty phase of the dye composition comprises one or more quaternary conditioning agents. Exemplary, but not exhaustive of such quaternary conditioning agents are materials that correspond to the general formula:

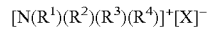

wherein $R^1$, $R^2$, $R^3$, and $R^4$ are independently selected from (a) an aliphatic group of from 1 to 22 carbon atoms or (b) an aromatic, alkoxy, polyoxyalkylene, alkylamido, hydroxyalkyl, aryl or alkylaryl group having up to 22 carbon atoms; and X is a salt-forming anion such as those selected from halide (e.g., chloride, bromide), acetate, citrate, lactate, glycolate, phosphate, nitrate, sulfate, and alkylsulfate radicals, wherein at least one of $R^1$, $R^2$, $R^3$, and $R^4$ is a hydrocarbyl chain having from 8 to 22 carbon atoms preferably alkyl. Salt-forming anions of particular interest are halides, preferably chloride. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. The conditioning quats may be used singly or in admixture.

Included among the suitable conditioning quats are mono- and dialkyl quats. Monoalkyl quats suitable for use herein include quaternary conditioning agents of the formula described above wherein $R^1$, $R^2$, and $R^3$, which may be the same or different, are $C_1$-$C_4$ alkyl groups, and $R^4$ is a $C_8$ or greater hydrocarbyl group (preferably $C_{14}$ to $C_{22}$ alkyl). The monoalkyl quats may, but need not, be in the form of mixtures. Non-limiting examples of monoalkyl quats are:

cetyltrimethylammonium chloride (C16);
stearyltrimethylammonium chloride (C18);
behenyltrimethylammonium chloride (C22);
cetyltrimethylammonium bromide (C16);
tallowtrimonium chloride (C16/C18);
behenyltrimethylammonium methosulfate (C22);
palmityltrimethylammonium chloride (C16);
hydrogenated tallowtrimethylammonium chloride (C16/C18);
hydrogenated tallowtrimethylammonium bromide (C16/C18);
hydrogenated tallowtrimethylammonium methosulfate (C16/C18);
cetrimonium tosylate (C16): and
eicosyltrimethylammonium chloride (C20).

Also included among the conditioning quats are dialkyl quats in which $R^1$ and $R^2$, which may be the same or different, are C1-C4 hydrocarbyl groups, preferably alkyl and $R^3$ and $R^4$, which may be the same or different, are C8 or greater alkyl groups (preferably C14 to C22) alkyl. If desired, mixtures of dialkyl quats may be used in the dye compositions of this invention. Non-limiting examples of dialkyl quats are:

dimethyldicetylammonium chloride (C16);
dimethyldistearylammonium chloride (C18);
dimethyldipalmitylammonium chloride (C16);
dimethyl(dihydrogenatedtallow)ammonium chloride (C16/C18);
dimethyl(ditallow)ammonium chloride (C16/C18)
dimethyl(dihydrogenatedtallow)ammonium bromide (C16/C18)
dimethyl(dihydrogenatedtallow)ammonium methosulfate (C16/C18)

Dialkyl quats of particular interest include mixtures of C16 and C18 dialkyl quats such as, for example, di(hydrogenated tallow)dimethylammonium chloride.

The conditioning quats are desirably present in the dye compositions of this invention in an amount of at least 0.5 wt. %, preferably from 1 to 10 wt. %. In at least one embodiment, the conditioning quat is present in the dye composition in an amount of from 2 to 8 wt %, more particularly from 2 to 6 wt %. Desirably, the ratio of fatty alcohol to quaternary conditioning agent is 4:1 to 0.5:1, preferably from 2.5:1 to 0.7:1. In at least one embodiment of this invention the ratio of fatty alcohol to conditioning quat is 2:1 to 1:1.

The hydroxypropyl starch phosphate is desirably present in the dye compositions of this invention in an amount of from 0.5 to 3.5 wt. %, preferably from 0.5 to 2 wt. %. In one embodiment of interest the hydroxypropyl starch phosphate is present in the dye composition an amount of from 0.7 to 1.5 wt. %, more particularly from 1 to 1.5 wt %. Hydroxypropyl starch phosphates are commercially available from suppliers that include National Starch and Grain Processing Corporation; suitable products include a National Starch hydroxypropyl starch phosphate available under the under the trademark Structure XL. In one embodiment, the hydroxypropyl starch phosphate is a corn starch based viscosity modifier produced by the hydroxypropylation of a waxy maize starch.

The dye composition further comprises, as a carrier therefor, water and at least one additional cosmetically acceptable solvent or diluent. Generally, the additional solvent or diluent is selected to be miscible with water. Included among the suitable solvents or diluents are mono- and polyhydric alcohols and their ethers, with the $C_1$-$C_{10}$ alcohols and ethers thereof and, in at least one embodiment of this invention, the $C_2$-$C_6$ alcohols and ethers thereof, being of particular interest. In one embodiment, preferred carriers for the dye component comprise water and, optionally, at least one additional .solvent selected from the group consisting of ethanol, ethylene glycol, propanol, isopropanol, glycerol, propylene glycol, butanol, and ethylene glycol monoethyl ether.

Desirably, the dye compositions of this invention further comprise one or more chelating agents. The term "chelating agent" (or "chelant" or "sequestering agent") is well known in the art and refers to a molecule or a mixture of different molecules each capable of forming a chelate with a metal ion. A chelate is an inorganic complex in which a compound (chelant) is coordinated to a metal ion at two or more points so that there is a ring of atoms including the metals. Chelants contain two or more electron donor atoms that form coordination bonds with the metal ion.

As used herein, the term "chelant" includes all salts and derivatives comprising the same functional structure as the parent chelant they are referring to that have similar or better chelating properties. The term "derivatives" also includes "chelating surfactant" compounds (these are chelants modified to bear a surfactant moiety while keeping the same chelating functionality, see U.S. Pat. No. 5,284,972, "N-acyl-N,N',N'-ethylenediaminetriacetic acid" for an example of modified ethylenediaminetriacetic acid). The term "derivatives" also includes large molecules comprising one or more chelating groups having the same functional structure as the partent chelants. An example of these large molecules is polymeric EDDS (ethylenediaminedisuccinic acid).

Preferred chelants for use herein are carboxylic acids, defined herein as chelants having at least one carboxylic acid moiety (—COOH) (in particular aminocarboxylic acids), phosphonic acids (in particular aminophosphonic acids), and polyphosphoric acids (in particular linear polyphosphoric acids), their salts and derivatives.

Examples of aminocarboxylic acid chelants suitable for use herein include nitrilotriacetic acid and polyaminocarboxylic acids such as diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N-N'-diglutaric acid (EDDG), 2-hydroxypropylenediamine-N-N'-disuccinic acid (HPDDS), ethylenediaminetetraacetic acid (EDTA), dipicolinic acid (DPA), salts thereof and derivatives thereof.

Other suitable aminocarboxylic chelants for use herein are iminodiacetic acid derivatives such as N-2-hydroxyethyl N,N diacetic acid or glyceryl imino diacetic acid (described in EP-A-317,542 and EP-A-399,133), iminodiacetic acid-N-2- hydroxypropyl sulfonic acid and aspartic acid N-carboxymethyl N-2-hydroxypropyl-3-sulfonic acid (described in EP-A-516,102), -alanine-N,N'-diacetic acid, aspartic acid-N,N'-diacetic acid, aspartic acid-N-monoacetic acid and iminodisuccinic acid chelants (described in EP-A-509,382), ethanoldiglycine acid, salts thereof and derivatives thereof.

EP-A-0 476 257 describes suitable amino based chelants. EP-A-0 510 331 describes suitable chelants derived from collagen, keratin or casein. EP-A-0 528 859 describes suitable alkyl iminodiacetic acid chelants. Dipicolinic acid and 2-phosphonobutane-1,2,4-tricarboxylic acid are also suitable.

Preferred aminocarboxylic chelants are diamine-N,N'-dipolyacid and monoamine monoamide-N,N'-dipolyacid chelants, salts thereof and derivatives thereof. Preferred polyacids contain at least two acid groups independently selected from the carboxylic, acid group (—COOH), sulfonic group (—SO$_3$H), the o-hydroxyphenyl group, the m-hydroxyphenyl group and the p-hydroxyphenyl group. Suitable polyacids include diacids, triacids and tetraacids, preferably diacids. Preferred salts include alkali metal, alkaline earth, ammonium or substituted ammonium salts. EDTA is a particularly preferred chelant.

Preferably, the polyacids are di-carboxylic acids, preferably di-carboxylic acids having a carbon chain length of from about 3 to about 10 carbon atoms, more preferably from about 4 to about 6 carbon atoms, even more preferably about 4 carbon atoms.

Exemplary diamine dipolyacids suitable for use herein include ethylenediamine-N,N'-disuccinic acid (EDDS), ethylenediamine-N,N'-diglutaric acid (EDDG), 2-hydroxypropylenediamine-N,N'-disuccinic acid (HPDDS), all disclosed in European Patent EP 0 687 292, ethylenedicysteic acid (EDC) disclosed in U.S. Pat. No. 5,693,854, diaminoalkyldi (sulfosuccinic acids) (DDS) disclosed in U.S. Pat. No. 5,472, 642 and EDDHA (ethylenediamine-N-N'-bis(ortho-hydroxyphenyl acetic acid)), a method of preparation of which is disclosed in EP 331,556. A preferred monoamine monoamide-N,N'-dipolyacid is glycinamide-N,N'-disuccinic acid (GADS), described in U.S. Pat. No. 4,983,315.

Highly preferred for use herein is ethylenediamine-N,N'-disuccinic acid (EDDS), derivatives and salts thereof. Preferred EDDS compounds for use herein are the free acid form, and salts thereof. Preferred salts include alkali metal, alkaline earth metals, ammonium and substituted ammonium salts (e.g. monoethanolammonium, diethanolammonium, triethanolammonium). Highly preferred salts are sodium, potassium, magnesium and calcium salts. Examples of such preferred sodium salts of EDDS include Na$_2$EDDS and Na$_3$EDDS.

Preferred aminocarboxylic acid chelants that are not diamine-N,N'-dipolyacid and monoamine monoamide-N,N'-dipolyacid chelants include N,N'-bis(2-hydroxybenzyl)ethylenediamine-N,N'-diacetic acid (HBED) salts thereof and derivatives thereof.

Suitable polyphosphoric acid type chelants include molecules that contain more than one P atom and have P—O—P bonds. Polyphosphoric acid chelants and salts (polyphosphates) can be linear and are generally represented by the formula $[P_nO_{3n+1}]^{(n+2)-}M_{(n+2)}^+$ wherein M is a suitable counter-ion such as H$^+$, Na$^+$ or K$^+$ and n an integer. Polyphosphoric acid type chelants and their polyphosphate salts can also be cyclic and have the formula $[P_nO_{3n}]^{n-}M_n^+$. Representative examples include, among others, sodium tripolyphosphate, tetrasodium diphosphates, hexametaphosphoric acid and sodium metaphosphate.

Suitable phosphonic acid type chelants include amino alkylene poly (alkylene phosphonic acid), ethane 1-hydroxy diphosphonic acids and nitrilo trimethylene phosphonic acids, salts thereof and derivatives thereof. Suitable chelants of this type are disclosed in U.S. Pat. No. 4,138,478, Reese et al., U.S. Pat. Nos. 3,202,579 and 3,542,918, Berth et al., all incorporated herein by reference.

Preferred chelants for use herein are aminotri-(1-ethylphosphonic acid), ethylenediaminetetra-(1-ethylphosphonic acid), aminotri-(1-propylphosphonic acid), and aminotri-(isopropylphosphonic acid).

Especially preferred chelants are aminotri-(methylenephosphonic acid), ethylene-diamine-tetra-(methylenephosphonic acid) (EDTMP) and diethylene-triamine-penta(methylenephosphonic acid) (DTPMP).

Chelant is present in the hair coloring compositions formed from the combination of the dye component and developer in an amount of at least about 1% by weight, more particularly from about 1 to about 5% weight percent, and preferably from about 1 to about 3% weight percent, based on the total weight thereof.

One or more additional ingredients such as conventionally used in the oxidation dye components of hair coloring system may be present in the dye compositions of this invention as optional components. Non-limiting examples of such ingredients include: viscosity modifiers, emulsifiers, fragrance components, surfactants, and the like.

Desirably, the dye compositions are formulated as emulsion compositions. The emulsion compositions may be formulated using standard preparative techniques such as are well known in the art. For example, the non-volatile, non-fatty phase components may be dissolved in the carrier, the non-volatile, fatty phase components added, and the resulting mixture heated to temperature sufficient to melt the fatty alcohol, typically, 70 to 90° C., followed by cooling to ambient temperature, with volatile components that may be present typically being added during cooling. Shearing the mixture during at least a portion of the heating and/or cooling stages of preparation provides a convenient means of emulsifying the fatty and non-fatty phases.

The developer with which the subject dye composition is mixed to form a hair coloring compositions comprises at least one peroxide-releasing compound as an oxidizing agent in a suitable cosmetically acceptable carrier. Normally, the peroxide-releasing compound is hydrogen peroxide or a source which generates this material or a hydroperoxyl radical, e.g., the ammonium, alkali and alkaline earth metal persulfates and perborates.

In order to stabilize the hydrogen peroxide that is present, the developer will normally be formulated to have a pH ranging from about 2 to about 5, preferably from 2.5 to 3.5. One or more buffering agents may be included within the developer to assist in maintaining a desired pH. Amounts of the buffering agents may from range from about 0.001 to about 2%, preferably from about 0.01 to about 0.1% by weight of the developer component. Phosphoric, hydrochloric, sulfonic and C$_2$-C$_{30}$ carboxylic acids and their salts are useful as buffering agents. Illustrative examples of buffering agents include but are not limited to: tartaric acid, citric acid, acetic acid, lactic acid, ammonium sulfate, sodium dihydrogen phosphate/phosphoric acid, potassium chloride/hydrochloric acid, potassium dihydrogen phthalate/hydrochloric acid, sodium citrate/hydrochloric acid, potassium dihydrogen citrate/hydrochloric acid, sodium tartarate/tartaric acid, sodium lactate/lactic acid, sodium acetate/acetic acid, disodium hydrogen phosphate/citric acid and sodium chloride/glycine/hydrochloric acid The developer may further comprise one or more additional optional ingredients such as are conventionally used in such compositions such as, for example, antioxidants, fragrances, pH adjusters, preservatives, viscosity modifiers, emulsifiers, and the like. The developer may be prepared by standard techniques known in the art.

In a hair coloring treatment according to the method of this invention, just prior to application the dye composition and developer are mixed together to form a hair coloring composition. In forming the hair coloring composition the dye composition and developer are typically combined in a ratio by weight of from 1:3 to 1:0.5, depending upon the formulation of the particular dye composition and developer employed. In the practice of this invention such ratios are commonly from about 1:2 to 1:1, with ratios of 1:1 being of particular interest in at least one embodiment. In one embodiment of this invention it is desired that the coloring composition contain less than 2 wt % of hydroxypropyl starch phosphate.

The resulting hair colorant composition is then applied to the hair, typically within a period that does not exceed 45 minutes after mixing. Optionally, the hair can be made wet prior to application of the coloring composition; preferably it is dry. Application temperatures are typically in the range of from about 15° C. to about 40° C. The colorant composition is allowed to remain on the hair for a period of from about 2 minutes to about 60 minutes, more particularly from about 5 minutes to about 30 minutes, depending upon the degree of coloration desired. The hair is then rinsed, preferably with water and/or a neutralizing agent. If desired, the hair may be subjected to one or more post-coloring conditioning treatments.

Kit Containing an Instruction Sheet

The present invention also relates to a kit for carrying out the hair coloring method of this invention. The kit comprises dye and developer as individually packaged components. By "individually packaged" it is meant that the components are contained in containers or packaging that allows them to be kept apart until just before use. The kit also includes written instructions that explain how the hair coloring compositions of the invention are prepared and used. Optionally, the kit may further comprise one or more post coloring treatment compositions such as for example, neutralizing solutions, shampoos and/or conditioners. Optionally, the kit may further comprise an additional optional component a mixing vessel for preparation of the hair coloring composition. Alternatively, the packaging for the dye composition or developer may be sized to accommodate the combination and mixing of the hair coloring composition components.

As used herein, the term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

EXAMPLES

The following examples will more fully illustrate the embodiments of this invention. All parts, percentages and proportions referred to here and elsewhere in the specification and the appended claims are by weight, unless specified otherwise.

Example 1

Dye compositions D1 through D5 were prepared according to the formulations described in Table 1. The dye compositions had pH values of approximately 10.6-10.7.

TABLE 1

| | Dye Compositions | | | | |
|---|---|---|---|---|---|
| Component (wt. %) | D1 | D2 | D3 | D4 | D5 |
| Water (Deionized) | QS to 100 | QS to 100 | QS to 100 | QS to 100 | QS to 100 |
| Cetrimonium Chloride | 1.70 | 1.70 | 1.70 | 1.70 | 1.70 |
| Dicetyldimonium Chloride | 2.10 | 2.10 | 2.10 | 2.10 | 2.10 |
| Stearyl Alcohol and Ceteareth-20 (30/70) | 1.00 | 1.00 | 1.00 | 1.00 | 1.00 |
| Cetyl Alcohol | 3.60 | 3.60 | 3.60 | 3.60 | 3.60 |
| Dimethicone | 0.10 | 0.10 | 0.10 | 0.10 | 0.10 |
| Cyclopentasiloxane (Dow Corning 245) | 1.80 | 1.80 | 1.80 | 1.80 | 1.80 |
| Fragrance | 0.80 | 0.80 | 0.80 | 0.80 | 0.80 |
| DMDM | 0.10 | 0.10 | 0.10 | 0.10 | 0.10 |
| Sodium Sulfite | 0.50 | 0.50 | 0.50 | 0.50 | 0.50 |
| Erythobic Acid | 0.08 | 0.08 | 0.08 | 0.08 | 0.08 |
| Disodium EDTA | 1.90 | 1.90 | 1.90 | 1.90 | 1.90 |
| Rodol D&J | 0.03 | 0.03 | 0.03 | 0.03 | 0.03 |
| Rodol RS | 0.02 | 0.02 | 0.02 | 0.02 | 0.02 |
| Rodol PMP | 0.02 | 0.02 | 0.02 | 0.02 | 0.02 |
| Rodol P | 0.20 | 0.20 | 0.20 | 0.20 | 0.20 |
| Rodol EG | 0.03 | 0.03 | 0.03 | 0.03 | 0.03 |
| Rodol Grey HED | 0.06 | 0.06 | 0.06 | 0.06 | 0.06 |
| $NH_4OH$ (28% active) | 12 | 12 | 12 | 12 | 12 |
| $(NH_4)_2CO_3$ | 15 | 15 | 7.4 | 15 | 15 |
| NaOH (50% active) | 13.2 | 13.2 | 6.1 | 13.2 | 13.2 |
| Structure XL[1] | — | — | — | 4.0 | 1.50 |
| Hydroxyethyl Cellulose | — | 1.50 | — | — | — |

[1]Hydroxypropyl Starch Phosphate from National Starch 200 ml samples (two sets) of dye compositions D1, D2, D3 and D5 were evaluated for storage stability. One set of samples was maintained at a temperature of 45° C. for a period of 2 weeks and a second set of samples was maintained at a temperature of 25° for a period of 2 weeks. The samples were then examined visually. The results of this storage stability testing is reported in Table 2, wherein "NO" indicates a lack of storage stability as evidenced by visible phase separation and "YES" indicates storage stability as evidenced by no visible phase separation.

TABLE 2

Storage Stability Data

| Dye Composition | Storage Stability at 25° C. | Storage Stability at 45° C. |
|---|---|---|
| D1 | No | No |
| D2 | No. | No |
| D4 | Yes | Yes |
| D5 | Yes | Yes |

As demonstrated by the Table 2 data, the hydroxypropyl starch phosphate-containing dye compositions (D4 and D5) had significantly better storage stability than either dye composition D2 (which lacked a hydroxypropyl starch phosphate, but contained hydroxyethyl cellulose) and D1 (which did not contain hydroxypropyl starch phosphate or hydroxyethyl cellulose).

Color lifting and conditioning were evaluated for test compositions prepared by mixing equal parts a selected dye composition as described in Table 1 (except that the dyes listed as present therein, i.e., Rodol D&J, Rodol RS, Rodol PMP, Rodol P, Rodol EG and Rodol Grey HED, were omitted and replaced with an otherwise identical amount of water) with an equal part by weight of a developer composition as described in Table 3.

Color lifting ability of the resulting test compositions (identified as TC3, TC4, and TC5) was evaluated using medium brown Caucasian hair tresses. Each tress was about 15 to about 20 cm in length and weighed about 5 g. For each hair coloring composition tested, 2 tresses were used; the two tresses were treated with approximately 10 g each of the test composition to be evaluated. The test composition was allowed to remain on the tresses for 40 minutes and then was removed by rinsing the tresses in water. The tresses were dried and then measured for changes in color intensity (dark to light) using a Hunter Colorimeter (Labscan XE Model) and the resulting ΔL values reported as an average for the 2 tresses. The procedure was repeated, with the tresses being subjected to a total of 3 bleaching treatments. Hunter ΔL values (average for two tresses) after 1 and 3 treatments are reported in Table 4 below.

Wet combing data was obtained on 15 medium brown Caucasian hair tresses that had been subjected to three bleaching treatments with a given test composition as identified in Table 4. Five panelists wet combed a series of 3 treated tresses (i.e. tresses treated with TC3, tresses treated with TC4, and tresses treated with TC5) and rated the ease of combing (conditioning) of the treated tresses on a scale of 1 to 4, with 4 being the highest conditioning rating and 1 being the lowest conditioning rating. Wet combing data is reported in Table 4 as the average of the 5 panelist ratings.

TABLE 3

Developer Composition

| Component | Wt. % |
|---|---|
| Deionized Water | 68.80 |
| Sodium Stannate | 0.01 |
| Phosphoric Acid, 85% | 0.02 |
| Stearamidopropyl Dimethylamine | 0.50 |
| Dicetyldimonium Chloride | 2.10 |

TABLE 3-continued

Developer Composition

| Component | Wt. % |
|---|---|
| Stearyl Alcohol and Ceteareth-20 | 1.00 |
| Cetyl Alcohol | 3.80 |
| Potassium Chloride | 0.10 |
| Disodium EDTA | 0.10 |
| Dimethicone | 0.10 |
| Cyclopentasiloxane | 1.80 |
| DMDM Hydantoin | 0.10 |
| Hydrogen Peroxide, 35% CG | 21.40 |
| Phosphoric Acid, 85% Active | 0.17 |

TABLE 4

Color Lift and Conditioning Data

| Test Composition | ΔL (1x) | ΔL (3x) | Wet Combing Score |
|---|---|---|---|
| TC3 (pH 10.5) - 1:1 mixture of D3 (modified as described above) and Developer. | 3.2 | 7.2 | 4 |
| TC5 (pH 10.5) - 1:1 mixture of D5 (modified as described above) and Developer. | 4.5 | 9.7 | 3.75 |
| TC4 (pH 10.5) - 1:1 mixture of D4 (modified as described above) and Developer. | 4.6 | 9.5 | 1 |

As demonstrated by the Table 4 data, Test Composition TC4 and TC5 (each having 7.5 wt. % ammonium carbonate) were more effective in their bleaching ability than Test Composition TC3 (3.7 wt. % ammonium carbonate). However, TC5 (0.75 wt. % hydroxypropyl starch phosphate) had significantly better conditioning performance than TC4 (2.0% hydroxypropyl starch phosphate). Thus, while storage stability of dye compositions containing relatively high levels of ammonium carbonate was shown to be improved by the addition of hydroxypropyl starch phosphate, a lower level of hydroxypropyl starch phosphate in the dye composition was demonstrated to significantly enhance conditioning performance in the resulting coloring composition.

What is claimed is:

1. A dye composition having a pH of from 9 to 11, the dye composition comprising:
    (a) oxidation dye precursor,
    (b) at least 8 wt % of carbonate salt,
    (c) from 4 to 15 wt % of a fatty phase comprising fatty alcohol and quaternary conditioning agent,
    wherein the quaternary conditioning agent comprises at least one quat of the formula:

$[N(R^1)(R^2)(R^3)(R^4)]^+[X]^-$ wherein $R^1$, $R^2$, $R^3$, and $R^4$ are independently selected from (a) an aliphatic group of from 1 to 22 carbon atoms or (b) an aromatic, alkoxy, polyoxyalkylene, alkylamido, hydroyalkyl, aryl or alkylaryl group having up to 22 carbon atoms; and X is a salt-forming anion, and wherein at least one of $R^1$, $R^2$, $R^3$, and $R^4$ is a hydrocarbyl chain having from 8 to 22 carbon atoms,
    (d) from 0.5 to 3.5 weight percent of hydroxypropyl starch phosphate, and
    (e) carrier,
    wherein the quaternary conditioning agent is present in the dye composition in an amount of at least 0.5 wt. % and the fatty alcohol and quaternary conditioning agent combined comprise from 60 to 100 wt % of the fatty phase, and wherein the ratio of fatty alcohol to quaternary conditioning agent is 4:1 to 0.5:1 and wherein the dye composition is free of peroxide and has a pH of at least 9.5.

2. A dye composition as describe in claim 1 wherein the carbonate salt is present in the composition in an amount of from 10 to 20 wt. %.

3. A dye composition as described in claim 1 wherein the carbonate salt comprises ammonium carbonate.

4. A dye composition as described in claim 3 wherein the carbonate salt further comprises an alkali metal carbonate.

5. A dye composition as described in claim 1 having a pH in excess of 9.5.

6. A dye composition as described in claim 1 wherein the quaternary conditioning agent is present in the dye composition in an amount of 1 to 8 wt. %.

7. A dye composition as described in claim 1 wherein the fatty alcohol is present in the dye composition an amount of 2 to 10 wt. %.

8. A dye composition as described in claim 1 which is an emulsion.

9. A dye composition as described in claim 1 wherein the carbonate salt is selected from the group consisting of ammonium carbonate, ammonium bicarbonate and ammonium carbamate.

10. A dye composition as described in claim 1 which further comprises at least one chelating agent.

11. A hair coloring composition formed by mixing a dye composition as described by claim 1 with a developer comprising at least one peroxide-releasing compound in a suitable cosmetically acceptable carrier, wherein the hair coloring composition contains less than 2 wt. % of hydroxypropyl starch phosphate.

12. A method of coloring hair using the hair coloring composition described in claim 11.

13. A hair coloring kit comprising as separately packaged components:
  (A) a dye composition as described by claim 1; and
  (B) a developer comprising at least one peroxide-releasing compound in a suitable cosmetically acceptable carrier,
wherein the kit further comprises directions instructing that the dye composition and developer are combined just prior to use to form a hair coloring composition, and wherein the dye composition and developer are formulated to be used at a weight ratio of dye composition to developer of from about 1:2 to 1:1.

* * * * *